United States Patent [19]

Kardon

[11] Patent Number: 5,490,098
[45] Date of Patent: Feb. 6, 1996

[54] AUTOMATED SYSTEM AND METHOD FOR DETERMINING PUPILLARY THRESHOLD RESPONSE

[75] Inventor: Randy H. Kardon, Iowa City, Iowa

[73] Assignee: University of Iowa Research Foundation, Oakdale, Iowa

[21] Appl. No.: 194,409

[22] Filed: Feb. 10, 1994

[51] Int. Cl.$^6$ .................................................. A61B 3/10
[52] U.S. Cl. .................... 364/580; 364/413.02; 351/200; 351/205; 351/224
[58] Field of Search .................. 364/413.01, 413.02, 364/413.04, 413.05, 580; 351/221, 226, 204, 205, 246, 210, 200, 224

[56] References Cited

U.S. PATENT DOCUMENTS

| | | | |
|---|---|---|---|
| 3,689,135 | 9/1972 | Young et al. | 351/246 |
| 3,966,310 | 6/1976 | Larson | 351/205 |
| 4,494,836 | 1/1985 | Cogez | 351/204 |
| 4,850,691 | 7/1989 | Gardner et al. | 351/221 |
| 5,035,500 | 7/1991 | Rorabaugh et al. | 351/226 |
| 5,042,937 | 8/1991 | Cornsweet | 351/204 |
| 5,050,983 | 9/1991 | Johnson et al. | 351/226 |
| 5,187,506 | 2/1993 | Carter | 351/221 |
| 5,204,703 | 4/1993 | Hutchinson et al. | 351/210 |
| 5,331,969 | 7/1994 | Silberstein | 364/413.05 |

OTHER PUBLICATIONS

Fairville Medical Optics, Inc. product literature for Pupilscan, dated Sep. 1, 1987 (4 pages).
Hamamatsu product literature for Iriscorder Model No. C2514, May 1990, (4 pages).
Hamamatsu Technical Sheet for Iriscorder C2514, Apr. 1988 (2 pages).
Hamamatsu product literature for Binocular Iriscorder Model No. C2515, Jun. 1986 (8 pages).
ISCAN product announcement for High Speed Eye Tracking & Pupillometry Systems, 1987 (2 pages).
ISCAN product announcement for Head Mounted Imaging System for Eye Movement Monitoring, 1987 (2 pages).
Skalar Medical product literature for IRIS A Significant Improvement in Infrared Light Reflection Eye–Tracking Systems, 1989 (4 pages).
Ikegami product literature for Model No. ICD–200 (undated) (2 pages).
Applied Science Laboratories Newsletter dated Apr. 1988 (4 pages).
Iconan product literature for I.R. Video Eng. System (undated) (4 pages).
OcutoKinetics, Inc. product description for EM/2 Alcohol & Drug Screener (undated) (3 pages).
"Noninvasive Assessment of The Visual System," *1990 Technical Digest Series*, vol. 3, Feb. 5–8, 1990, Incline Village, Nevada.
Myers et al., "Eye Monitor, Microcomputer–Based Instrument Uses an Internal Model to Track the Eye," *Computer*

(List continued on next page.)

*Primary Examiner*—Emanuel T. Voeltz
*Assistant Examiner*—M. Kemper
*Attorney, Agent, or Firm*—Woodard, Emhardt, Naughton Moriarty & McNett

[57] ABSTRACT

An automated system and method for determining pupillary threshold response is described. The system achieves the determination of pupillary threshold levels through the measurement of supra-threshold responses at varying light intensities, which measured values are processed by a non-linear regression routine to approximate threshold response. The system takes supra-threshold measurements by means of a computerized pupillometer which is linked to an automated perimeter. The measurements are sequentially taken at varied light intensities which are reiteratively selected in response to the comparison between responses that have been previously measured during the test and a pre-stored response curve of expected values. The measured values are then processed by a non-linear regression routine to indirectly generate an estimated threshold level. The system is fully automated, produces accurate and reliable results, and is not subject to the uncertainties which are attendant with the measurement of threshold levels by the taking of subjective measurements.

4 Claims, 2 Drawing Sheets

OTHER PUBLICATIONS pp. 14–21, Mar. 1991.

Kardon et al., "Automated Pupil Perimetry, Pupil Field Mapping in Patients and Normal Subjects," *Ophthalmology* 98(4):485–496, Apr. 1991.

Interzeag AG Pupil Perimeter Octopus 1–2–3 Instruction Manual, Mar. 1992.

Roecker et al., "Characterization of the Electroretinographic Scotopic B–Wave Amplitude in Diabetic and Normal Subjects," *Investigative Ophthalmology & Visual Science* 33 (5):1575–1583, Apr. 1992.

AUTOMATED SYSTEM AND METHOD FOR DETERMINING PUPILLARY THRESHOLD RESPONSE

BACKGROUND OF THE INVENTION

1. Field of the Invention

This invention relates to the measurement of pupillary threshold response in the eye.

2. Description of the Prior Art

One of the major problems facing the ophthalmologist today is how to detect blinding eye disease early, decide on the cause, and institute treatment before significant visual loss occurs. Many of the conditions affecting the optic nerve and retina are treatable; these include glaucoma, compressive optic neuropathy (from tumors, aneurysms, or Graves Disease), pseudotumor cerebri (idiopathic intracranial hypertension), proliferative diabetic retinopathy, retinal detachment, and forms of aging macular degeneration.

Unfortunately, the present methods available for screening for these diseases are not very satisfactory. Patients with early eye disease are frequently asymptomatic and their diagnosis is often dependent upon a careful ophthalmologic examination. Even then, early signs may go undetected. Difficult and time consuming tests of visual function are often necessary to make the correct diagnosis, but they too can be normal early in the disease process. Furthermore, important tests of visual function, such as those that assess visual acuity, visual fields, color vision, and contrast sensitivity are typically subjective in nature. In addition, many patients are not capable of accurately responding to subjective test measurements, as their judgment is often so clouded by their fears of blindness that their responses tend to be unreliable. Thus, visual tests which are based upon subjective measurement are inherently lacking in accuracy or reliability.

Wherefore, there is a need for an improved system for assessing visual loss that is more objective, efficient and reliable. This invention makes use of an objective neuronal reflex, the movement of the eye's pupil in response to light stimuli, in order to better assess visual function. Computerized methods of providing carefully controlled light stimuli and precise recording of pupil movements in response to light are used to quantify the pupillary light reflex. The present invention uses new methods to determine the threshold light intensity needed for a pupillary response (pupil threshold). The system of the present invention is based upon objective rather than subjective measurements, can be completed in a short period of time, and provides accurate and reliable results.

SUMMARY OF THE INVENTION

The present invention provides an automated system and method for determining pupillary threshold response. The system achieves the determination of pupillary threshold levels through the measurement of supra-threshold responses at varying light intensities, which measured values are processed by a non-linear regression technique to approximate threshold response. The system takes supra-threshold measurements by means of a computerized pupillometer which is linked to an automated perimeter. The measurements are sequentially taken at varied light intensities which are selected on a reiterative basis as a result of a comparison between pupil responses measured during the test and pre-stored response curves of expected response values. The measured values are then processed by a non-linear regression routine to indirectly generate an estimated threshold level. The system is fully automated, produces accurate and reliable results, and is not subject to the uncertainties which are attendant with the measurement of threshold levels by the taking of subjective measurements.

DESCRIPTION OF THE PREFERRED EMBODIMENT

Figure 1:
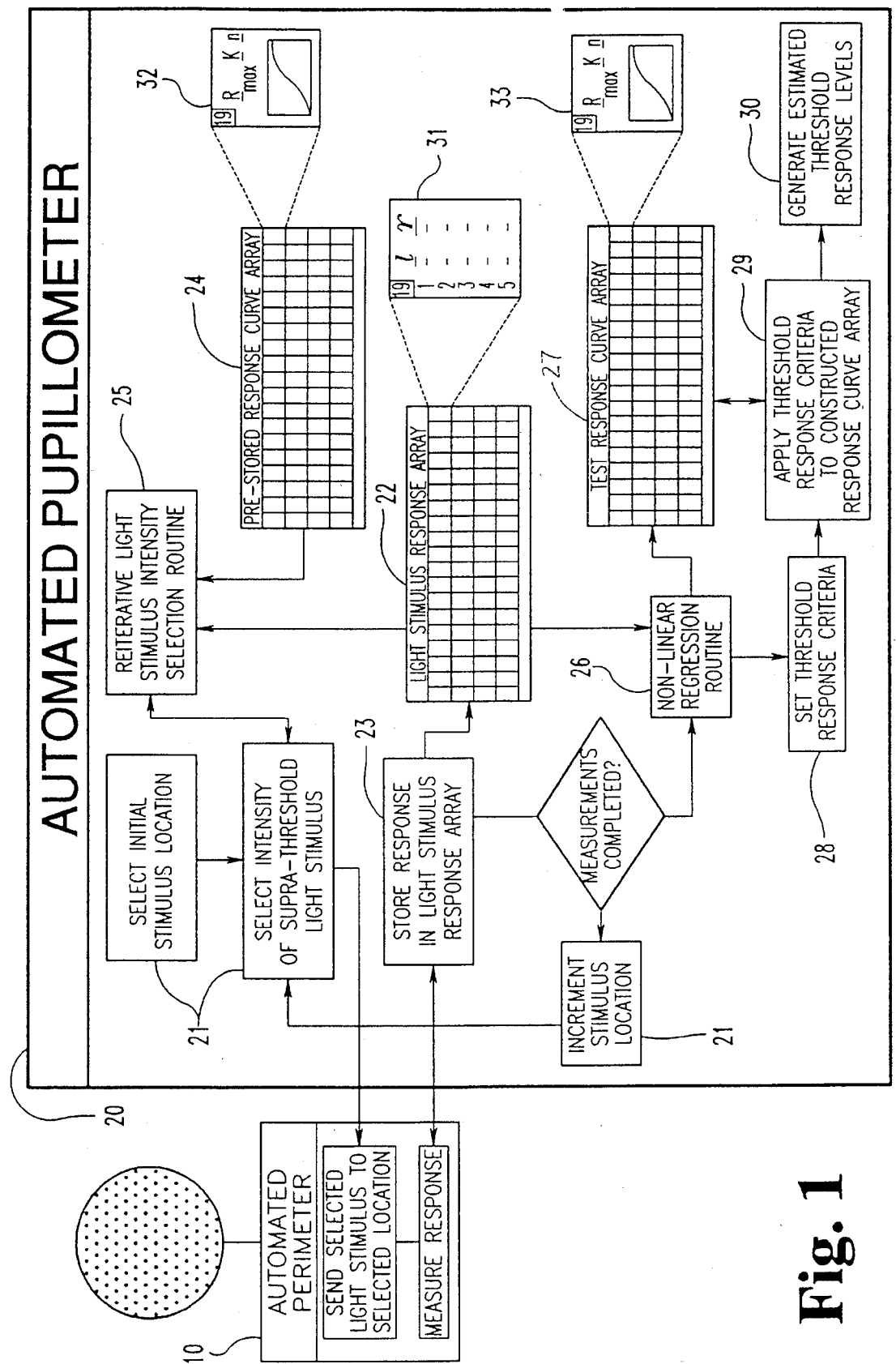
FIG. 1 is a schematic representation of a system of the present invention for determining pupillary threshold response levels based upon the taking of supra-threshold measurements.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

There will now be described an automated system and method for determining pupillary threshold response through the measurement of supra-threshold responses at varied light intensities. The system takes supra-threshold measurements by means of a computerized infrared pupillometer which is linked to an automated perimeter, and sequentially exposes the eye to varied light intensities which are determined by a reiterative routine which compares responses that have been previously measured during the test to expected responses based upon a pre-stored response curve array. The measured values are then processed by a non-linear regression routine to approximate the threshold response level.

A system according to the present invention is schematically shown in FIG. 1. As shown in this drawing, automated perimeter 10 includes means for exposing the eye to light over a range of intensities at a number of locations about the visual field and measuring pupillary response thereto. Automated pupillometer 20 operates to control the operation of automated perimeter 10 and processes measured responses received therefrom. Automated pupillometer 20 includes, as shown in FIG. 1., means 21 for selecting and instructing automated perimeter 10 to expose the eye at each of a given number of locations to an initial light stimulus which is substantially above the expected threshold level at said location. Automated pupillometer 20 further includes light stimulus response array 22, means for receiving measured responses received from automated perimeter 10 and storing the measured responses into light stimulus response array 23. Pre-stored response curve array 24 stores expected pupillary responses to a range of light intensities at each of said given number of locations. Reiterative light stimulus intensity selection routine 25 sequentially determines subsequent light intensities to be applied to the eye by automated perimeter 10 at each of said given locations based upon a comparison between responses that have been previously measured during the test and expected responses derived from pre-stored response curve array 24 for each given location. Non-linear regression analysis routine 26 then constructs a test response curve array 27 from the measured responses that have been stored in light stimulus response array 23. Means for setting threshold response criteria 28, and means for applying a selected threshold response criteria to test response curve array 29 and for generating estimated threshold response levels therefrom 30 are also provided.

Figure 2A:
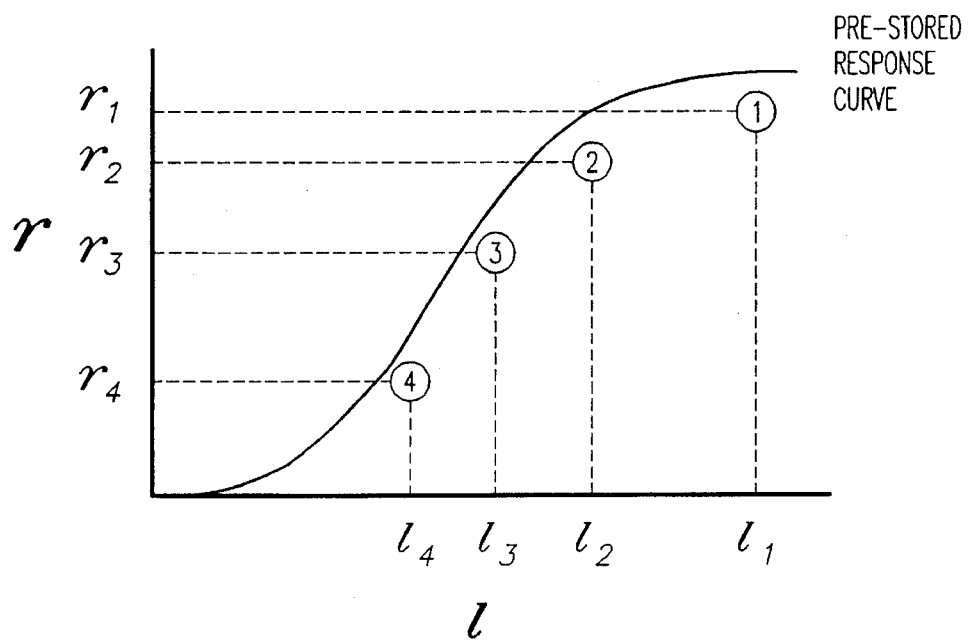
FIG. 2a is a graph showing sequential test measurements in comparison with a pre-stored response curve.

The process of reiterative light stimulus intensity selection routine 25 is illustrated in FIG. 2a. In this figure, sequential test measurements 1, 2, 3 and 4 are graphically shown in comparison with a pre-stored response curve. Each sequential test measurement is compared with a pre-stored response curve by reiterative light stimulus intensity selection routine 25 as a factor in determining the light intensity to be applied in the next subsequent test measurement. Separate curves are stored for each location to compensate for the fact that pupillary response sensitivity varies over the visual field. In this way, the sigmoidal curve structure of actual pupillary response can be most accurately approximated with only a few test measurements. It is estimated that reliable test measurements can be achieved through this technique by the taking of only 4 or 5 test measurements at each location.

Non-linear regression routine 26 includes a "curve fitting" routine which is applied to characterize the stimulus-response curve over the range of stimulus intensities that have been applied. A non-linear regression fit can thus be produced onto a sigmoidal curve described by the equation:

$$R = \frac{R_{max} \rho^n}{\rho^n + K^n}$$

where R is the response amplitude, $R_{max}$ is the maximum response amplitude, l is the stimulus luminance, K is the half saturation constant (the intensity at half $R_{max}$), and n is a dimensionless parameter that determines the slope of the non-linear sigmoidal fit. The three parameters, $R_{max}$, K, and n thus serve to characterize the shape of the curve.

Figure 2B:
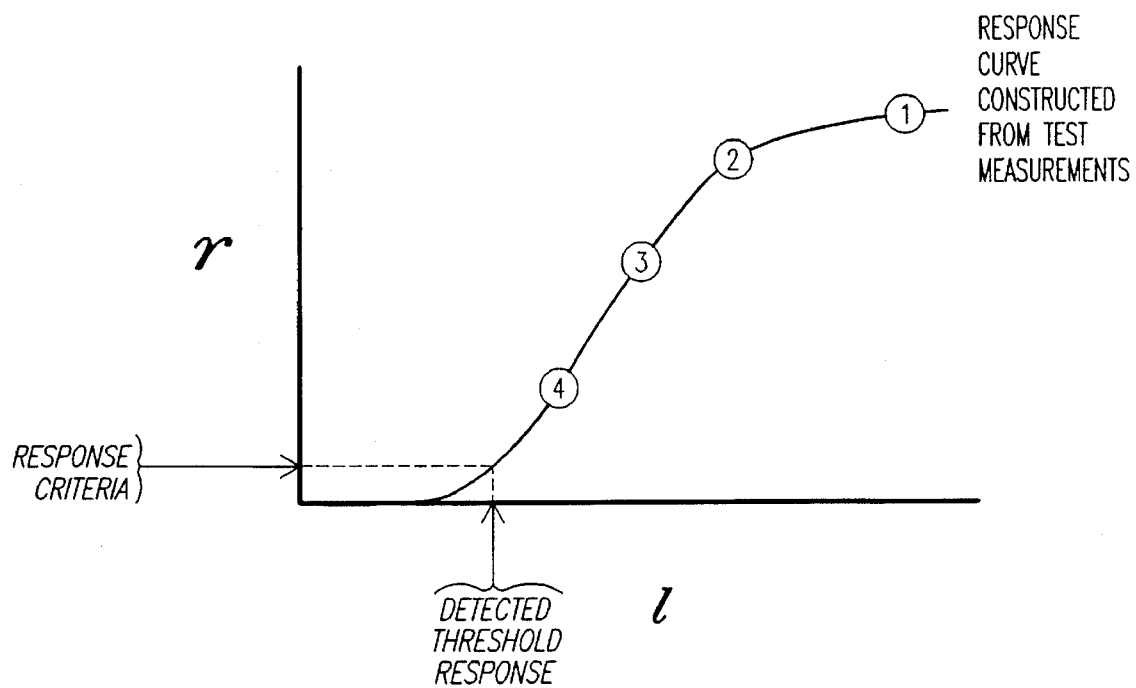
FIG. 2b is a graph of a test response curve that has been constructed through non-linear regression analysis from test measurement points. Also shown on FIG. 2b is the detection of threshold response by the application of a response criteria to the test response curve.

FIG. 2b is a graph of a test response curve that has been constructed through non-linear regression analysis from test measurement points 1, 2, 3, and 4. Also shown on FIG. 2b is the detection of threshold response by the application of a response criteria to the test response curve.

The system of the present invention can be adopted to test for any of a variety of suitable pupillary response parameters. Pupillary contraction amplitude, maximum velocity of pupillary contraction, and pupil latency time are three such parameters which are considered well suited for use in the system of the present invention. The system may also be performed with the use of small area focus points, as illustrated herein, or by the application of full field light exposures.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A computerized system for determining pupillary threshold response based upon the taking of supra-threshold measurements, said system comprising:

automated perimeter means for exposing the eye to light over a range of intensities at a number of locations in the visual field around the eye and measuring pupillary response thereto; and automated pupillometer means for controlling the operation of said automated perimeter means and for processing measured responses received therefrom, said automated pupillometer means including:

means for selecting and instructing said automated perimeter means to expose the eye at each of said given number of locations to an initial supra-threshold light stimulus which is substantially above the expected threshold level at said location;

a light stimulus response array;

means for receiving measured responses received from said automated perimeter means and storing said measured responses in said light stimulus response array;

a pre-stored response curve array of expected pupillary responses to a range of light intensities at each of said given number of locations;

reiterative light stimulus intensity selection routine means for sequentially determining subsequent supra-threshold light intensities to be applied to the eye by said automated perimeter means at each of said given locations based upon a comparison between previously measured responses stored in said light stimulus response array and expected responses derived from said pre-stored response curve array for said given location;

non-linear regression analysis routine means for constructing a test response curve array from said measured responses stored in said light stimulus response array;

means for setting threshold response criteria; and means for applying said threshold response criteria to said test response curve array and for generating estimated threshold response levels therefrom.

2. The computerized system for determining pupillary threshold response of claim 1 in which said means for measuring pupillary response includes means for measuring pupillary contraction amplitude.

3. The computerized system for determining pupillary threshold response of claim 1 in which said means for measuring pupillary response includes means for measuring maximum velocity of pupillary contraction.

4. The computerized system for determining pupillary threshold response of claim 1 in which said means for measuring pupillary response includes means for measuring pupil latency time.

* * * * *

UNITED STATES PATENT AND TRADEMARK OFFICE
CERTIFICATE OF CORRECTION

PATENT NO. : 5,490,098
DATED : February 6, 1996
INVENTOR(S) : Randy H. Kardon

It is certified that error appears in the above-identified patent and that said Letters Patent is hereby corrected as shown below:

In column 3, line 35, please delete "ρ" and insert in lieu thereof --*l'*--.
In column 3, line 37, please delete "ρ" and insert in lieu thereof --*l'*--.
In column 3, line 40, please delete "1" and insert in lieu thereof --*l'*--.
In column 4, line 45, please start a new paragraph after "and".

Signed and Sealed this

Fourth Day of June, 1996

Attest:

BRUCE LEHMAN

*Attesting Officer*     *Commissioner of Patents and Trademarks*